United States Patent [19]

Haag et al.

[11] Patent Number: 4,487,972

[45] Date of Patent: Dec. 11, 1984

[54] PRODUCTION OF OXYGENATED COMPOUNDS

[75] Inventors: Werner O. Haag, Lawrenceville; Darrell D. Whitehurst, Titusville, both of N.J.

[73] Assignee: Mobil Oil Corporation, New York, N.Y.

[21] Appl. No.: 142,788

[22] Filed: Apr. 22, 1980

Related U.S. Application Data

[60] Continuation of Ser. No. 815,872, Jul. 14, 1977, abandoned, which is a division of Ser. No. 107,863, Jan. 19, 1971, Pat. No. 4,098,727, which is a continuation-in-part of Ser. No. 57,796, Jul. 23, 1970, abandoned, and a continuation-in-part of Ser. No. 860,807, Sep. 24, 1969, abandoned, and Ser. No. 672,009, Oct. 2, 1967, , said Ser. No. 860,807, is a continuation-in-part of Ser. No. 672,010, Oct. 2, 1967, , said Ser. No. 57,796, is a continuation-in-part of Ser. No. 672,008, Oct. 2, 1967, abandoned.

[30] Foreign Application Priority Data

Sep. 26, 1968 [GB] United Kingdom ............... 45771/68

[51] Int. Cl.$^3$ ..................... C07C 45/50; C07C 29/16
[52] U.S. Cl. ..................... 568/444; 568/429; 568/454; 568/455; 568/311; 568/342; 568/387; 568/715; 568/909; 568/821; 568/826; 562/459; 562/508; 562/577; 562/69; 260/465 R; 260/465.1; 564/305; 564/502; 208/16

[58] Field of Search ............... 568/909, 454, 429, 455, 568/311, 444, 342, 387, 715, 821, 826; 562/459, 508, 577, 41, 69; 260/465 R, 465.1; 564/305, 502

[56] References Cited

U.S. PATENT DOCUMENTS

| | | | |
|---|---|---|---|
| 3,636,159 | 1/1972 | Solomon | 568/455 |
| 3,824,221 | 7/1974 | Ragg | 525/326 |
| 3,825,601 | 7/1974 | Rennick | 568/454 |
| 3,847,997 | 11/1974 | Allen | 568/453 |
| 3,998,887 | 12/1976 | Allen | 568/17 |

*Primary Examiner*—Bernard Helfin
*Attorney, Agent, or Firm*—A. J. McKillop; M. G. Gilman; L. P. Hobbes

[57] ABSTRACT

This specification discloses a process for the production of oxygenated compounds, more specifically aldehydes and alcohols, by reacting an olefin with hydrogen and carbon monoxide in the presence of, as a ctalyst, an insoluble polymer containing a functional group, which may be an amine, thiol, phosphine, or arsine group, having chemically bonded thereto a metal of Group VIII of the Periodic Table. The metal can be, for example, rhodium, cobalt, or ruthenium. The olefin can contain more than one carbon-to-carbon double bond, may be an open chain or a cyclic olefin, and may be substituted. Further, the olefin may be contained in a refinery stream such as a cracked gasoline. The reaction may be carried out in the presence of a polar solvent.

7 Claims, No Drawings

4,487,972

PRODUCTION OF OXYGENATED COMPOUNDS

CROSS REFERENCES TO RELATED APPLICATIONS

This application is a continuation of copending application Ser. No. 815,872 filed July 14, 1977 and now abandoned, which in turn is a division of application Ser. No. 107,863 filed Jan. 19, 1971 and now U.S. Pat. No. 4,098,727.

Application Ser. No. 107,863 is a continuation-in-part of our copending application, Ser. No. 57,796, filed July 23, 1970 and now abandoned. This latter application is a continuation-in-part of our earlier application, Ser. No. 672,008, filed Oct. 2, 1967, and now abandoned, which earlier application was copending with said latter application.

Application Ser. No. 107,863 is also a continuation-in-part of our copending application Ser. No. 672,009, filed Oct. 2, 1967, and our copending application Ser. No. 860,807, filed Sept. 24, 1969 and now abandoned. This latter application is a continuation-in-part of our earlier application, Ser. No. 672,010, filed Oct. 2, 1967, and now abandoned, which earlier application was copending with said latter application.

Application Ser. No. 860,807 discloses the hydroformylation of an olefin by reacting it with hydrogen and carbon monoxide in the presence of a catalyst to produce aldehydes and alcohols. Its parent application, Ser. No. 672,010, also disclosed the hydroformylation of an olefin by reacting it with hydrogen and carbon monoxide in the presence of a catalyst.

The production of an alcohol by reacting an aldehyde or an acetal (including a hemiacetal) with hydrogen in the presence of carbon monoxide in the presence of catalysts disclosed in this application is disclosed and claimed in our copending application, Ser. No. 107,852 filed concurrently with this application Applicant claims priority under 35 U.S.C. 119 to British patent application No. 45771/68, filed Sept. 26, 1968 in Great Britain, which claim to priority was also made in application Ser. No. 860,807, filed Sept. 24, 1969.

BACKGROUND OF THE INVENTION

1. Field of the Invention

This invention relates to the production of aldehydes and alcohols and relates particularly to the production of these oxygenated compounds by reacting an olefin with hydrogen and carbon monoxide in the presence of a catalyst.

2. Description of the Prior Art

The reaction of an olefin with hydrogen and carbon monoxide is the well-known hydroformylation reaction. It is also known as the oxo reaction. Catalysts employed for this reaction have included cobalt and rhodium carbonyls which are soluble in the reaction mixture when the reaction is carried out in the liquid phase. Soluble ruthenium catalysts have also been used. Additionally, cobalt and rhodium contained in crystalline alumina-silicates, these being insoluble in the liquid reaction mixture, have been suggested.

In the prior art processes of reacting an olefin with hydrogen and carbon monoxide, the use of homogeneous metal-containing catalysts, i.e., soluble in the liquid reaction mixture, has presented difficulties. The recovery and regeneration of the dissolved metal catalysts from the liquid reaction products require special equipment and handling which add significantly to the complexity and cost of the operations. Furthermore, small losses in recovering, regenerating, and recycling the soluble catalysts are unavoidable. In the case of expensive catalysts, especially those containing rhodium, these losses increase the cost of the operation substantially and to a point where the operation may not be economically justified.

Means have heretofore been sought to overcome the disadvantages inherent in the use of homogeneous catalysts. For example, it has been proposed to use metals such as rhodium or cobalt on a solid support, as disclosed in the article by Pruett et al., Journal of Organic Chemistry, Vol. 34, p. 327 (February, 1969). However, in these instances, the active catalyst, believed to be a metal carbonyl complex, is formed from the metal under the reaction conditions, and the complex is soluble in the liquid reaction medium. It has also been proposed, as in U.S. Pat. No. 3,352,924, to use as a solid catalyst in the hydroformylation reaction a crystalline alumina-silicate containing rhodium or cobalt ions. However, such catalysts, when used in a continuous operation, lose their initial activity after some time and then cease to function. It has been further proposed to deposit selected rhodium complexes on particles of inert solids such as carbon, silica, clays or metal oxides, for example, by impregnation, as in U.S. Pat. No. 3,487,112, to produce a hydroformylation catalyst. Under the conditions of the hydroformylation reaction, however, the complexes, and their carbonyl reaction products, are soluble in the liquid reaction medium.

The disadvantages inherent in the use of homogeneous catalysts can be avoided by carrying out the reactions in the gas phase. This, however, limits the type of reactants, or reaction conditions, or both, that may be employed. Thus, since the hydroformylation reaction occurs at quite low temperatures, a severe restriction is imposed on the usable partial pressure of the reagents, and of the products. It also limits the reaction to reactants of low boiling point and low molecular weight.

Further, with respect to various of the above-mentioned catalysts and others heretofore employed, difficulty has been encountered by the reaction being insufficiently selective to conversion of the olefin to aldehyde or alcohol, a significant portion of the olefin feed being hydrogenated to form a saturated compound.

SUMMARY OF THE INVENTION

In accordance with the invention, there is provided a process for the production of aldehydes and alcohols. An olefin is reacted with hydrogen and carbon monoxide in the presence of a catalyst. The catalyst is characterized as being an insoluble polymer containing a functional group having chemically bonded thereto a metal of Group VIII of the Periodic Table.

DESCRIPTION OF THE PREFERRED EMBODIMENTS

In the process of the invention, the catalyst is essentially insoluble in the reaction mixture. The metal portion of the catalyst is chemically bonded to the polymer portion. Being chemically bonded to the polymer portion, the metal portion is strongly bonded to the polymer portion. These bonds are not readily severed and the metal readily resists solution in the reaction mixture. Moreover, the polymer portion of the catalyst is insoluble. By "insoluble" is meant that the polymer is insoluble in common solvents and, in particular, is insoluble in the reactants and reaction products in the reaction mixture. The catalyst, therefore, can be used in liquid phase operations for long periods of times. Further, the use of these catalysts allows for greatly simplified processing of the reaction products to recover the catalyst and the desired components with resulting economic advantages. With respect to the catalyst containing certain of the Group VIII metals such as rhodium or ruthenium, the invention enables use of these metals which are ordinarily too expensive for use in the production of aldehydes and alcohols. Moreover, in the process of the invention, there is a selective production of aldehydes and alcohols. Stated otherwise, the predominant reaction is the production of aldehydes and alcohols with competing reactions being at a minimum. Thus, hydrogenation of the olefin to form a saturated hydrocarbon is at a minimum. Furthermore, hydrogenolysis of the hydroxyl group of the alcohol is insignificant.

The polymer portion of the catalyst may be provided by any solid, insoluble polymer that is capable of containing a functional group. Preferably, the polymer is an organic polymer. Suitable polymers include copolymers such as those of styrene and a divinylbenzene compound, for example, a styrene-divinylbenzene copolymer. Other suitable polymers include resins such as phenol-aldehyde, for example, phenol-formaldehyde, melamine-formaldehyde, urea-formaldehyde, polyalkylene-formaldehyde, and polystyrene resins. Cellulose polymers can also be used. It is preferred that the polymer portion of the catalyst be intrinsically porous.

Functional groups contained by the polymer portion of the catalyst include amine, thiol, phosphine, or arsine groups. Preferred groups are tertiary amine and phosphine groups. The tertiary amine groups may be monoamine, diamine, or triamine groups. The nitrogen atom in these amine groups may be substituted with aromatic or aliphatic groups or it may be part of a heterocyclic ring system such as pyridine, quinoline, thiazoles, diazoles, triazoles, oxazoles, pyrimidine, imidazole, purine, methylindole, pyrazine, adenine, and uracil. Tertiary amine groups containing at least one, two, or better, three aliphatic alkyl groups are preferred. Particularly preferred tertiary amine functional groups are those whose soluble analogs have a base strength measured as $pK_b$ of from 3 to 7. Phosphine groups may be those having the formula, $R_1R_2R_3P$, where $R_1$, $R_2$, and $R_3$ are the same or different and may be H or alkyl or aryl groups. Preferred phosphine groups are tertiary phosphines where all three R's are alkyl or aryl.

The attachment of the functional group to the polymer is a conventional procedure. Accordingly, a detailed discussion of the procedure is not believed necessary. However, it may be stated that these procedures involve appropriate chemical treatment of the polymer. For example, a styrene-divinylbenzene copolymer may have an amine functional group attached thereto by first chloromethylating the polymer and subsequently reacting it with the amine. The resulting product comprises the polymer with the nitrogen of the amine chemically bound to a carbon atom which in turn is attached to a carbon atom of a benzene ring of the polymer. Further, for example, a styrene-divinylbenzene copolymer containing a phosphine functional group may be obtained by reacting the copolymer with phosphorus trichloride. The phosphorus chemically binds to a carbon atom of a benzene ring of the copolymer. The copolymer may be subjected to further chemical action to substitute an organic radical for the remaining chlorine atoms attached to the phosphorus.

The metal portion of the catalyst may be any metal of Group VIII of the Periodic Table. These metals are iron, cobalt, nickel, ruthenium, rhodium, palladium, osmium, iridium, and platinum. Preferred metals are cobalt, ruthenium, and rhodium. Rhodium is particularly preferred.

The metal portion of the catalyst is bonded to the functional group. Procedures for bonding are disclosed in the aforementioned applications, Ser. Nos. 672,009 and 860,807. These procedures include reacting the polymer containing the functional group with a complex compound of the metal, the complex compound comprising the metal and at least two ligands. One of the ligands exchanges with the polymer containing the functional group, i.e., ligand exchange, thereby chemically bonding the metal to the polymer through the functional group.

It has been found to be particularly effective to carry out the hydroformylation reaction in the presence of an added polar solvent. Marked increases in the rates of aldehyde and alcohol formation are encountered depending upon the type of solvent employed. The magnitude of the rate enhancement is a function, however, of the catalyst and the nature of the solvent.

Solvents that may be employed include aromatic hydrocarbons, ethers, esters, ketones, nitriles, amines, phenols, hydroxylamines, sulfones, carboxylic acids, phosphorus- and sulfur-containing acids, alcohols, and water. Preferred solvents are those containing hydroxyl groups. Especially preferred solvents are water and alcohols. The alcohols may be primary, secondary, or tertiary and may be substituted or unsubstituted. The substituents may be hydrocarbons, halides, amines, sulfides, ethers, esters, carboxylic acids and others. Lower molecular weight alcohols are more effective than higher molecular weight alcohols. Specific solvents that may be employed include isobutyl alcohol, butyl ether, benzene, triethylamine, acetonitrile, 3-pentanone, methanol, hexanol, and acetic acid. The choice of a particular solvent is determined, among other factors, by its effectiveness to bring about a desired rate enhancement. Its choice is also determined by the ease with which it can be separated from the reaction products. Thus, it is preferred to employ a solvent which has a boiling point below that of the oxygenated hydrocarbon reaction products so that it may be separated from the reaction products simply by distillation. The alcohol product can be used as the solvent. Water as an added solvent has the special advantage of easy separation from the reaction products where these are not miscible with water to any extent.

The concentration of the added solvent in the reaction mixture will affect the rate of the reaction. However, a leveling effect occurs in some cases. Major activity increases occur up to about 6 to 10 volumes percent where the solvent is an alcohol. Concentrations greater than this, while giving activity increases, give proportionally smaller increases. However, large concentrations of alcohols do not harm the overall catalyst performance and may be desirable to aid in heat removal.

The use of an added solvent has another advantage. As mentioned previously, it is preferred that the polymer portion of the catalyst be intrinsically porous. Porosity of the polymer portion of the catalyst imparts increased activity to the catalyst. With catalysts having an organic polymer portion which is not intrinsically porous, porosity may be induced into the polymer portion by solvent swelling. Various of the solvents mentioned above will effect swelling of the polymer portion of the catalysts. These solvents include the alcohols such as isobutyl alcohol. The increased activity of the catalyst achieved from swelling of the polymer portion of the catalyst will be a function of a number of variables including the degree of swelling.

In the process of the invention, any suitable olefin may be employed. These olefins may have the formula:

$$R_1-CR_2=CR_3-R_4, \tag{1}$$

in which $R_1$, $R_2$, $R_3$, and $R_4$ can be hydrogen or a group such as an alkyl, cycloalkyl, aryl, acyl, nitrile, halogen, alkoxy, hydroxy, carboxy, ester, keto, amine, or thio group. Each R can be the same as or different from any other R. Suitable illustrative olefins include ethylene, propylene, the butenes, pentenes, hexenes, heptenes, octenes, nonenes, decenes, undecenes, dodecenes, tetradecenes, pentadecenes, hexadecenes, octadecenes, eicosenes, hexacosenes, and triacontenes. These may be straight or branched chain olefins with the double bond in the 1-position or any other position. Olefin oligomers are useful, such as propylene tetramer, isobutylene trimer, propylene pentamer, isobutylene tetramer, and propylene hexamer.

Other suitable olefins are open chain, conjugated, or unconjugated diolefins having 3 to 20 or 30 or more carbon atoms, and including allene, butadiene, isoprene, pentadiene, hexadiene, heptadiene, diisobutenyl, decadiene, and the like and substituted diolefins such as 2-cyanobutadiene and chloroprene. Also of use are open chain olefins having more than two double bonds, sometimes designated oligo-olefins, such as hexatriene and 2,6-dimethyl-2,4,6-octatriene. Cyclic olefins, which may be multicyclic, such as bicyclic or tricyclic, are suitable. Included among such olefins are cyclopropene, cyclobutene, cyclopentene, cyclohexene, cycloheptene, cyclooctene and terpenes such as the various menthenes, camphenes, thujenes, carenes, pinenes, and bornylenes and cyclic diolefins and cyclic oligo-olefins such as cyclopentadiene, fulvene, norbornadiene, cyclooctadiene, 4-vinylcyclohexene, limonene, dipentene, dicyclopentadiene, cycloheptatriene, cyclooctatriene, bicyclo(2.2.2.)octa-2,5,7-triene, cyclonona-1,4,7-triene and cyclooctatetraene. A feature of the invention is the fact that, when employing an olefin containing more than one double bond, an unsaturated alcohol, di- or tri-alcohols, or compounds containing both an aldehyde group and an alcohol group can be obtained.

The olefin subjected to reaction with the hydrogen and carbon monoxide in the presence of the catalyst may be in a substantially pure state or may be mixed with other olefins. Further, the olefin or mixture of olefins may be contained in a mixture with another compound, or other compounds, of a non-olefinic nature. In accordance with another specific embodiment of the invention, the olefin subjected to reaction with the hydrogen and carbon monoxide in the presence of the catalyst is contained in a refinery stream, which refinery stream contains components of a non-olefinic nature.

The use of a refinery stream is doubly advantageous. Firstly, it is economically desirable to employ inexpensive commercial mixtures of olefins. Such olefinic mixtures are potentially available in plentiful supply in the form of various refinery streams. Secondly, various of these refinery streams, such as a cracked gasoline, contain certain low boiling constituents such as pentenes and possibly hexenes whose removal has been suggested to reduce the emission of reactive, volatile hydrocarbons from automobiles and hence reduce air pollution. Treatment of such refinery streams by the process of the invention reduces the olefinic content of the refinery streams. The olefins are converted to useful aldehydes and alcohols. These may be readily separated from the unreacted constituents of the refinery stream by simple distillation. Alternatively, they may be left in the refinery stream to be used, for example, where the stream is a cracked gasoline, as a gasoline blending component of improved quality from the standpoint of air pollution.

It is a particular feature of the catalyst that it is relatively unaffected by various impurities that are found in refinery streams. These impurities include dienes and sulfur compounds and their removal has been heretofore necessary before hydroformylation of the refinery stream with certain catalysts could be carried out. Thus, their removal has been necessary where the conventional cobalt carbonyl catalyst has been employed. On the other hand, the catalyst employed in the process of the invention is not affected by dienes and, in fact, the dienes, as pointed out above, are included among the olefins which may be employed for the production of aldehydes and alcohols. Further, the presence of small amounts of sulfur in the olefin feed has little or no effect on the rate of conversion of the olefins or on the lifetime of the catalyst even when used for extensive periods of time. Other impurities found in commercial, unpurified refinery streams, such as phenols and nitrogen and phosphorous compounds, have no deleterious effect on the catalyst. Further, these compounds are not hydrogenated in the presence of the catalyst.

Refinery streams which may be employed include fuel gas, propane-propene, butane-butene, light gasoline, and heavy gasoline streams. Fuel gas streams consist predominantly of hydrocarbons containing one and two carbon atoms and, where produced by thermofor catalytic cracking, contain approximately 20 mole percent of olefin. Propane-propene, butane-butene, light gasoline, and heavy gasoline streams consist predominantly of hydrocarbons containing three carbon atoms, four carbon atoms, five and six carbon atoms, and seven to eleven carbon atoms, respectively. Their olefin content, where the streams are produced by thermofor catalytic cracking, is, respectively, approximately 60, 30, 30, and 20 mole percent. These refinery streams typically contain mixtures of aliphatic and aromatic compounds in addition to the olefin compounds. The higher olefins are primarily internal and the carbon skeletons are linear, branched, or cyclic. Dienes are generally present and compounds containing nitrogen, sulfur or phosphorus occur in small amounts.

Another refinery stream which may be employed is that resulting from wax cracking. Wax cracking produces streams containing a wide molecular weight range of olefins and these are mostly linear terminal olefins. Other olefin-containing refinery streams which may be employed are obtained from naphtha cracking and from coke ovens.

Referring to the conduct of the reaction of the olefin with the hydrogen and carbon monoxide in the presence of the catalyst, a range of reaction conditions may be employed. Thus, liquid hourly space velocities (LHSV) from 0.1 to 30 volumes of olefin charge per volume of catalyst per hour, temperatures from 50° to 250° C., and pressures from 70 to 4400 pounds per square inch (psi) may be employed. The mole ratio of carbon monoxide to olefin may be from 1 to 20 and the mole ratio of hydrogen to carbon monoxide may be from 0.33 to 10.

Reaction conditions and catalyst may be selected to favor the production of either alcohols or aldehydes at the expense of the other. For example, a more selective production of aldehydes is favored by employing a catalyst comprising rhodium bound to a polymer containing phosphine functional groups. Further, this more selective production of aldehydes is favored by shorter reaction times, i.e., higher space velocities, lower ratios of hydrogen to carbon monoxide, i.e., ratios of 1:1 and less, and temperatures below 200° C. Also, for example, a more selective production of alcohols is favored by employing a catalyst comprising rhodium bound to a polymer containing amine functional groups. Moreover, this more selective production of alcohols is favored by longer contact times, i.e., lower space velocities, higher ratios of hydrogen to carbon monoxide, i.e., ratios of 2:1 and higher, temperatures of 80° C. or higher, and higher pressures. Additionally, more selective production of alcohols is favored by using alcohols as added solvents.

Following completion of the hydroformylation reaction, the aldehydes and alcohols can be separated from the reaction mixture by distillation. The aldehydes and alcohols will have a higher boiling point than the olefin reactant, and any isomers formed, and the carbon monoxide and hydrogen are gaseous at normal conditions of temperature and pressure. The alcohols and aldehydes can also be separated from each other by distillation since, ordinarily, the aldehydes will boil at temperatures from 20°–40° C. lower than the corresponding alcohols. Generally, any of the procedures heretofore employed for working up the reaction mixture from a hydroformylation reaction may be employed.

The following examples will be illustrative of the invention. Of these examples, the first eight will be illustrative of the preparation of catalysts which may be employed in the practice of the process of the invention. The remaining examples will be illustrative of the results obtained by the process of the invention.

EXAMPLE 1

This example will illustrate the preparation of a catalyst comprising rhodium bound to a styrene-divinylbenzene copolymer containing phosphine functional groups.

For the preparation of this catalyst, an intrinsically porous insoluble cross-linked styrene-divinylbenzene copolymer was employed. This copolymer had a porosity of 0.35 ml (milliliter) of pore space per ml of solid polymer, a surface area of 100 square meters per gram (g) on the dry basis, an average pore diameter of 205 Angstrom units, an average particle size of 0.35 millimeter, and a skeletal density of 1.06 g per ml. One liter of the polymer was cleaned by chromatographically washing with 5 liters of distilled water, 4 liters of methanol, and 4 liters of benzene. The adsorbed solvents were then removed from the polymer by evaporation in a rotary evaporator at 70° C. in vacuo. The yield of dry material was 442 g.

The washed dry polymer, in the amount of 440 g, was placed into a flask equipped with a reflux condenser along with 886 g (6.40 moles) of phosphorus trichloride and 1 liter of 1,1,2,2-tetrachloroethane as a solvent. The resultant reaction mixture was heated to the reflux temperature (about 96° C.) and solid anhydrous aluminum chloride was added in portions over a period of 6 hours. At the end of this time, a total of 594 g (4.45 moles) of aluminum chloride had been added. After heating for 9 hours, the mixture was allowed to cool to room temperature and permitted to remain at this temperature overnight.

The polymer was removed from the reaction mixture by filtration and was stirred with refluxing 1,1,2,2-tetrachloroethane for 16 hours. The polymer was removed and stirred with fresh hot solvent for an additional 1 hour. The polymer was again removed. The resultant polymer was a chlorophosphonated styrene-divinylbenzene copolymer.

A 100 ml aliquot of the chlorophosphonated copolymer was removed and washed with benzene, hexane, and diethyl ether. It was then suspended in 500 ml of diethyl ether, and 150 ml of 2.8 molar butyl lithium in hexane were added to the suspension. The suspension was allowed to react at ambient temperature for 2 hours. The reaction mixture was then mixed with 1 liter of methanol and allowed to stand overnight. The polymer was separated from the remainder of the reaction mixture by filtration and washed with each of the following solvents in sequence: methanol, distilled water, 2Normal (N) hydrochloric acid, 2N sodium hydroxide, distilled water, methanol, and benzene. The polymer was then dried at 70° C. in a rotary evaporator in vacuo. The dried weight of the product was 35 g and contained phenyldibutylphosphine functional groups. The amount of phosphorus, on a weight basis, was 10% of the product.

Twenty g of the product were suspended in 300 ml of benzene containing 3.609 g of tristriphenylphosphine rhodium chloride. The suspension was heated to the reflux temperature for 2 hours, then transferred to an autoclave, and the reaction was continued for 4 hours at 100° C., and at a total pressure of 1000 pounds per square inch gage (psig) of a 1:1 mixture of carbon monoxide and hydrogen. The resulting catalyst was then isolated by filtration, washed with benzene, and dried on a rotary evaporator at about 70° C. in vacuo. The yield of the catalyst was 20.9 g and contained, on a weight basis: phosphorus-9.70%, rhodium-1.02%, and chlorine-1.13%.

EXAMPLE 2

This example will be illustrative of the preparation of a catalyst comprising rhodium bound to a styrene-divinylbenzene copolymer containing phenyldibutylphosphine functional groups.

For the preparation of this catalyst, the procedure of Example 1 was followed up to the point of producing the product containing the phenyldibutylphosphine functional groups. This product, in the amount of 162 g, was suspended in 1 liter of benzene containing 3 g of tristriphenylphosphine rhodium (I) chloride and the mixture was heated to 65° C. under an atmosphere of a 1:1 molar ratio of hydrogen and carbon monoxide. The reaction was allowed to proceed for about 18 hours. The resultant catalyst was removed by filtration, under an atmosphere of hydrogen and carbon monoxide, from the solvent containing excess reagent and byproducts. The solid catalyst was washed with four 1-liter portions of hot benzene and was then dried in vacuo. This catalyst contained, on a weight basis: phosphorus-9.55%, rhodium-0.33%, and chlorine-0.95%.

EXAMPLE 3

This example will further illustrate the preparation of a catalyst comprising rhodium bound to a styrene-divinylbenzene copolymer containing phenyldibutylphosphine functional groups.

For the preparation of this catalyst, the procedure of Example 1, similarly as in Example 2, was followed up to the point of producing the product containing the phenyldibutylphosphine groups. This product, in the amount of 100 g, was suspended in 400 ml of 95% ethanol and the resultant mixture was stirred and heated to the reflux temperature. Carbon monoxide was then passed through the suspension for the duration of the catalyst preparation. Rhodium trichloride trihydrate, $RhCl_3 \cdot 3H_2O$, in the amount of 2.51 g was dissolved in 100 ml of warm 95% ethanol. This solution was then added to the polymer suspension and the mixture was allowed to react for 1 hour. The mixture was cooled and the resultant catalyst was removed by filtration. The catalyst was washed with 95% ethanol and diethyl ether and then dried. The catalyst contained, on a weight basis: phosphorus-6.76%, rhodium-0.65%, and chlorine-1.19%.

EXAMPLE 4

This example will illustrate the preparation of a catalyst comprising cobalt bound to a styrene-divinylbenzene copolymer containing benzyldimethylamine functional groups.

For the preparation of this catalyst also, the procedure of Example 1 was followed up to the point of producing the product containing the phenyldibutylphosphine functional groups. This product in the amount of 10 g was suspended in 100 ml of benzene in a reaction flask and the flask was flushed with nitrogen. To the suspension were added 25 ml of a benzene solution containing 1.71 g of dicobalt octacarbonyl. The resulting mixture was then heated to 50°–60° C. and allowed to react for about 6 hours. During this time, evolution of carbon monoxide occurred, the solution became colorless, and the polymer became green, indicating that the cobalt had become chemically bound to the polymer. The solvent was removed by filtration and the polymer was washed with benzene. On drying, the catalyst weighed 11.3 g. Its composition on a weight basis was: phosphorus-8.77% and cobalt-4.82%.

EXAMPLE 5

This example will illustrate the preparation of a catalyst comprising ruthenium bound to a styrene-divinylbenzene copolymer containing amine functional groups.

Fifty g of an intrinsically porous copolymer composed of cross-linked styrene-divinylbenzene containing benzyldimethylamine functional groups were added to a solution of 2.0 g of triruthenium dodecacarbonyl dissolved in 500 ml of benzene. The resultant suspension was heated to the reflux temperature and maintained at this temperature for about 4 hours. During this time, carbon monoxide was evolved. The resultant catalyst was isolated by filtration, washed with 1 liter of benzene and dried in a vacuum oven at 110° C. The catalyst contained about 2% by weight of ruthenium chemically bound to the amine groups of the polymer.

EXAMPLE 6

This example will further illustrate the preparation of a catalyst comprising rhodium bound to a styrene-divinylbenzene copolymer containing benzyldimethylamine functional groups.

A finely ground cross-linked styrene-divinylbenzene copolymer containing benzyldimethylamine functional groups, in the amount of 16 g, was moistened with absolute ethanol. Rhodium trichloride trihydrate, in the amount of 2 g, was dissolved in 100 ml of absolute ethanol and the solution heated to 50° C. The copolymer was then added to the solution and the resulting mixture was stirred at temperature for about 1 hour at which time the solution became colorless. The resulting catalyst was filtered from the solution, washed with absolute ethanol and dried at 110° C. for 1 hour. Analysis showed the catalyst contained, on a weight basis: rhodium-5.83% and chlorine-5.33%.

EXAMPLE 7

This example will illustrate the preparation of another catalyst comprising rhodium bound to a styrene-divinylbenzene copolymer containing benzyldimethylamine functional groups.

Rhodium trichloride trihydrate, in the amount of 10.3 g, was dissolved in 1700 ml of water containing 12 g of sodium chloride. The resulting solution was heated to 50° C. and to it were added 200 g of 18–50 mesh cross-linked styrene-divinylbenzene copolymer containing benzyldimethylamine functional groups. The mixture was stirred for 16 hours at 50° C. During this time, the solution became colorless. The mixture was cooled and the resulting catalyst removed therefrom by filtration. The catalyst was washed successively with water, methanol, and benzene and then dried on a rotary evaporator in vacuo at 50° C. Analysis showed the catalyst to contain on a weight basis: rhodium-1.42%, chlorine-2.23%, and sodium-0.03%.

EXAMPLE 8

This example will illustrate the preparation of a catalyst comprising rhodium bound to an ion exchange cellulose containing tertiary amine functional groups.

Rhodium carbonyl chloride, $Rh_2(CO)_4Cl_2$, in the amount of 0.1887 g, was dissolved in 200 ml of benzene and 10.0 g of a commercially available, weakly basic ion exchange cellulose containing tertiary amine functional groups, identified as DEAE Cellulose, were added to the solution. The mixture was stirred at room temperature until the solution became colorless. The benzene solvent was then removed by evaporation in vacuo. The resultant catalyst was composed of rhodium carbonyl chloride bound to the tertiary amine functional groups of the ion exchange cellulose and had the following analysis on a weight basis: carbon-43.6%, hydrogen-7.1%, rhodium-0.58% and chlorine-0.36%.

EXAMPLE 9

This example will illustrate the results obtained by the hydroformylation of various olefins.

In each of the reactions in this example, a continuous, fixed bed flow reactor was employed. Further, in each of the reactions, the catalyst was packed in a tubular flow reactor and olefin, hydrogen, and carbon monoxide were passed concurrently continuously over the catalyst. The catalysts employed were those prepared in accordance with Examples 1, 2, and 3. The conversions and selectivities which are set forth in the table below were obtained, as in all of the subsequent examples where a continuous, fixed bed flow reactor was employed, by analyses of the steady-state composition of the reactor eluate. Table I gives the olefin employed, the catalyst, the temperature and pressure, the molar styrene-divinylbenzene copolymers containing rhodium bound to either tertiary amine or tertiary phosphine groups. In some of the reactions, benzene or methanol was employed as a solvent. The olefins, the catalyst, the solvent, the reaction conditions and the results obtained are given in Table II.

TABLE II

| | Type of Polymer[a] | Added Solvent | Weight Ratio Olefin/ Catalyst | Reaction Time (hrs.) | Temp °C. | Pressure (psi) | Molar Ratio $H_2/CO$ | % Conversion of the Olefin | % Selectivity to Aldehyde |
|---|---|---|---|---|---|---|---|---|---|
| Camphene | P | Benzene | 24.9 | 52.6 | 98 | 1060 | 1 | 81.6 | 96.2[b] |
| Camphene | A | Methanol | 18.0 | 22.3 | 115 | 1200 | 2 | 57.8 | 91.5[b] |
| beta-Pinene | A | Methanol | 31.7 | 19.8 | 99 | 1280 | 2 | 80.4 | 13.7[b,c] |
| d-Limonene | P | — | 61.3 | 20.6 | 111 | 1300 | 1 | 81.1 | 61.8[d] |
| Dicyclopentadiene | P | — | 46.8 | 18.4 | 105 | 1125 | 1 | 82.3 | 85[d] |
| 2,5-Dimethyl-1,5-hexadiene | A | Methanol | 30.3 | 70.8 | 110 | 1100 | 2 | 54.2 | 57[d] |

[a]A = tertiary amine and P = tertiary phosphine.
[b]The bicyclic carbon skeleton in the product was found to be unchanged.
[c]The major byproduct was alpha-pinene (71.6%).
[d]This selectivity represents the percent monounsaturated aldehyde found in the product.

ratio of carbon monoxide, hydrogen, and olefin, the liquid hourly space velocity (LHSV), the percent conversion of olefin, and the percent selectivity to aldehydes. By "percent selectivity to aldehydes" is meant the mole percent of aldehydes in the olefin conversion products. It will be observed from the table that, with the catalysts and conditions employed, aldehydes were the main products of the reactions.

TABLE I

| Olefin | Catalyst | Temp (°F.) | Pressure (psi) | Molar Ratio $CO/H_2$/Olefin | LHSV | % Conv. of Olefin | % Selectivity to Aldehydes |
|---|---|---|---|---|---|---|---|
| 1-Hexene | Example 1 | 190 | 1550 | 1.25/1.25/1 | 2 | 87 | 99+ |
| 2-Hexene | " | 200 | " | " | 2 | 25 | 99+ |
| Cyclohexene | " | 199 | " | " | 2 | 4.8 | 99+ |
| 2-Methyl-2-pentene | " | 200 | " | " | 2 | 5.5 | 99+ |
| Light TCC gasoline | Example 2 | 245 | 1550 | 3/3/1 | .16 | 84 | 99 |
| 1-Octene | Example 3 | 214 | 1000 | 1.1/1.1/1 | 2.5 | 67 | 98.5 |
| Propylene | " | 182 | 2000 | " | 2 | 29.9 | 99.1 |
| | " | 354 | " | " | 2 | 94.5 | 98.8 |
| | " | 229 | 500 | " | 1 | 27.2 | 96.8 |

EXAMPLE 10

This example will illustrate the conversion of ethylene to propionaldehyde.

Into a 300 ml stirred autoclave were placed 4.3 g of a catalyst comprising 1.4%, by weight, of rhodium bound to a cross-linked styrene-divinylbenzene copolymer containing tertiary amine functional groups. This catalyst was prepared by a procedure similar to that described in Example 7. Into the autoclave were also placed 75 ml of cyclohexane. The autoclave was heated to 100° C. and charged with a 1:1:1 mole ratio mixture of ethylene, carbon monoxide, and hydrogen such that a constant pressure of 1000 psi was maintained. After 5 hours, the autoclave was cooled to room temperature and vented. The yield of liquid product was 16.8 g. It contained 89.5% propionaldehyde, 5.0% propanol, and 4.2% diethylketone.

EXAMPLE 11

This example illustrates the results obtained employing dienes and terpenes.

In this example, the reactions were carried out in a rocking autoclave and the catalysts were cross-linked

EXAMPLE 12

This example will illustrate the lifetime of the catalyst employed in the process of the invention.

In this example, the catalyst as prepared in Example 1 was employed. Into a tubular flow reactor were placed 6 g of the catalyst. 1-Hexene was passed downflow over the catalyst at a rate of 32 ml per hour, along with hydrogen and carbon monoxide, at a total pressure of 1560 psi and at a temperature of 90±5° C. Under these conditions, liquid phase operation took place. The molar ratios of the hydrogen, carbon monoxide, and hexene were 1.25:1.25:1. A mixture of linear and branched chain heptanals was produced at a ratio of 69.31 in 99% selectivity. During continuous operation for 22 days, the conversions ranged from 88% to 78%. Thus, for 22 days of liquid phase operation, the catalyst maintained substantial conversion activity.

EXAMPLE 13

This example will illustrate the loss of activity encountered with certain prior art catalysts.

The reaction of Example 12 was repeated except that catalysts made by impregnating porous alumina with tristriphenylphosphine rhodium chloride or by impregnating porous alumina with chlorocarbonyl bis(triphenylphosphine)rhodium (I) were employed. The catalysts lost all activity within a few hours due to elution of rhodium compounds from the alumina.

EXAMPLE 14

This example will illustrate the results obtained employing a catalyst comprising cobalt bound to a styrene-divinylbenzene copolymer containing phosphine functional groups. It will also illustrate the operative life of the catalyst and the retention of the metal in the polymer.

In this example, the catalyst of Example 4 was employed. In a tubular flow reactor were placed 10.2 g of the catalyst. 1-Hexene at a rate of 18 ml per hour was passed downflow over the catalyst together with hydrogen and carbon monoxide at a total pressure of 2000 psi and a temperature of 120° C. The molar ratios of reactants were $2.5/2.5/1 = H_2/CO/hexene$, respectively. After 1.25 hours of operation, the conversion of hexene was found to be 1.7% and it produced primarily heptylaldehydes. After 24 hours of operation, the conversion was found to be unchanged at 1.7%. The temperature was raised to 143° C. and the conversion increased to 2.3%. After an additional 12 hours at this temperature, the conversion was found to be unchanged at 2.3%. The continuous flow operation was continued for a total of 84 hours with essentially no loss in catalytic activity. The reactor was dismantled and the catalyst was recovered. Analysis of the recovered catalyst showed that it contained 4.6% cobalt or 95.8% of the cobalt originally charged. Thus, the catalyst was operative for extended periods of time with very little loss of activity or cobalt.

EXAMPLE 15

This example will compare the effect of a hydroformylation catalyst of the prior art with that of the catalyst employed in the preceding example.

The prior art catalyst employed in this example was a crystalline alumina-silicate containing cobalt. It was prepared in accordance with the procedures set forth in U.S. Pat. No. 3,352,924 and was composed of a Y-type zeolite in its cobalt form and had the following analysis on a weight basis: silicon dioxide ($SiO_2$)-65.9%, aluminum oxide ($Al_2O_3$)-20.3%, cobalt (Co)-9.65%, sodium (Na)-2.79%, and chlorine (Cl)-<0.01%.

In a tubular reactor were placed 12.2 g of the catalyst (1.17 g cobalt). 1-Hexene at a rate of 20 ml per hour was passed downflow over the catalyst together with hydrogen and carbon monoxide at a total pressure of 2000 psi and a temperature of 125° C. The molar ratio of reactants were $2.5/2.5/1 = H_2/CO/hexene$, respectively. After 3.5 hours of operation, the conversion of hexene was found to be 18%, producing primarily heptylaldehydes. The activity of this catalyst rapidly decreased and, after 23 hours of operation, the conversion had dropped to 1.1%. This amounts to a 95% loss in activity in 23 hours. Further decrease in conversion occurred with continued use. Cobalt was eluted from the catalyst during the operation and the observed activity closely paralleled the concentration of soluble cobalt carbonyls in the eluate.

After 26 hours of operation, the reactor was dismantled and the catalyst was recovered. Analysis of the recovered catalyst showed that it contained 7.62% by weight of cobalt. Thus, although about 79% of the original cobalt was retained on the used catalyst, it was practically inactive as a hydroformylation catalyst.

EXAMPLE 16

This example will illustrate the effect of a catalyst comprising ruthenium bound to a styrene-divinylbenzene copolymer containing benzyldimethylamine functional groups.

In this example, the catalyst of Example 5 was employed. An autoclave was charged with 9.6 g of the catalyst and 100 ml of 1-hexene. The contents of the autoclave were then heated to 101° C. and a 50/50 mixture of carbon monoxide and hydrogen was added to give a pressure of 1000 psi. After 85 minutes, the temperature was raised to 121° C. The pressure was maintained between 900 and 1000 psi by periodic addition of the carbon monoxidehydrogen mixture. After 19 hours, a sample of the reaction mixture was withdrawn and analyzed by vapor phase chromatography. This analysis showed that the product mixture had the following composition on a molar basis: hexane-3.0%, 1-hexene-1.5%, 2- and 3-hexenes-72.9%, n-heptanal-13.0%, isomeric heptylaldehydes-6.3%, and heptylalcohols-2.9%.

It will be seen, therefore, that the catalyst promotes hydroformylation to produce primarily aldehydes along with some alcohols. It also promotes olefin isomerization and, to a lesser extent, olefin hydrogenation.

EXAMPLE 17

This example will further illustrate the effect of a catalyst comprising rhodium bound to a styrene-divinylbenzene copolymer containing benzyldimethylamine functional groups.

In this example also, the catalyst of Example 5 was employed. An autoclave was charged with 3 g of the catalyst and 100 ml of 1-hexene. The contents of the autoclave were then heated to 100° C. and a 50/50 mixture of carbon monoxide and hydrogen was added to give a pressure of 1000 psi, and the pressure was maintained between 200 and 1000 psi by periodic addition of the carbon monoxide-hydrogen mixture. After 90 minutes, a sample of the reaction mixture was withdrawn and analyzed by vapor phase chromatography. This analysis showed that about 70% of the hexene had been converted to a mixture of heptanal and 2-methyl hexanal which were present in the respective ratio of about 3:1. Isomeric hexenes were also identified.

The reaction was allowed to proceed for a total of 1000 minutes and another sample was withdrawn. On analysis of this sample by vapor phase chromatography, it was found that 89% of the hexenes had been converted to products. In addition to heptanals, 5.3% of the products were heptylalcohols. Only small amounts of these alcohols were noted in the previous sample. Thus, with longer reaction time, the production of alcohols was substantially increased.

EXAMPLE 18

This example, similar to Example 17, will further illustrate the effect of a catalyst comprising rhodium bound to a styrene-divinylbenzene copolymer containing benzyldimethylamine functional groups.

Again, the catalyst of Example 5 was employed. The catalyst was screened to obtain particles of 20-30 mesh, and 38.6 g of the particles were placed in a tubular fixed bed flow reactor and heated to 80°-96° C. A mixture of $H_2$, CO, and 1-hexene was continually passed over the catalyst in a respective molar ratio of 2.2:1.1:1 at a total pressure of 2000 psi. The volume of liquid feed passing over the catalyst per hour was 33 ml. Under these conditions, the conversion of the olefins was 90% and the effluent composition on a molar basis was as follows: hexene-10.0%, heptylaldehyde-0.3%, and heptylalcohol-89.7%. Thus, at a conversion of 90%, the selectivity to alcohol was 99.7%. The recovered hexene consisted of isomerized olefins, i.e., 2- and 3-hexene. The heptylalcohol was a mixture of the following: n-heptanol-63%, and 2-methyl hexanol plus 3-ethyl pentanol-37%.

This catalyst was used continuously for 45 days with essentially no loss in activity.

EXAMPLE 19

This example will illustrate the effect of variation in process conditions on the production of alcohols.

In this example, a catalyst similar to that of Example 7 and 1-hexene were employed and the reactions were conducted in a tubular, fixed bed continuous flow reactor. The reaction conditions and the results obtained are given in the table.

TABLE III

| Temp. (°F.) | Pressure (psi) | $H_2/CO/$ Olefin | LHSV | % Conv. | % Selectivity to Alcohol |
|---|---|---|---|---|---|
| 239 | 500 | 2/1/1 | 0.33 | 34.4 | 29.9 |
| 241 | 950 | 2.2/1.1/1 | 0.33 | 66.4 | 89.9 |
| 195 | 1500 | 2.2/1.1/1 | 0.33 | 80.2 | 97.8 |
| 242 | 1500 | 2.2/1.1/1 | 0.33 | 88.0 | 98.3 |
| 238 | 2000 | 2.7/1.35/1 | 1.04 | 76.8 | 96.7 |

EXAMPLE 20

This example will illustrate the effect of catalysts comprising rhodium bound to styrene-divinylbenzene copolymers containing various amine functional groups. All the reactions were carried out in a 300 ml stirred autoclave pressured to 1000 psi with a 1:1 mixture of carbon monoxide and hydrogen at 102±3° C. The functional group, the relative activity for aldehyde production ($A_{CHO}$), and the percent alcohol at 80% conversion (% Alc), i.e., the percent of alcohol found in the product mixture at 80% conversion of the 1-hexene, are given in the table.

TABLE IV

| Functional Group | $A_{(CHO)}$ | % Alc |
|---|---|---|
| Pyridine | 1.0 | 3.4 |
| Phenyldimethylamine | 1.0 | 5.0 |
| Benzyldimethylamine | 29 | 26 |
| Phenylethyldimethylamine | 28 | 1-2 |
| Trimethylamine | 8.3 | — |
| Tetramethylethylenediamine | 23 | 67 |

EXAMPLE 21

This example will illustrate the effect of the catalyst of Example 6 on the hydroformylation of 2-hexene.

An autoclave was charged with 3 g of the catalyst and 100 ml of 2-hexene. The contents of the autoclave were then heated to 100° C. and a 50/50 mixture of carbon monoxide and hydrogen was added to give a pressure of 1000 psi, and this pressure was maintained between 600 and 1000 psi by periodic addition of the carbon monoxide-hydrogen mixture. After 2.1 hours, a sample of the reaction mixture was withdrawn and analyzed by vapor phase chromatography. This analysis showed that the reaction mixture had the following composition on a molar basis: 1-hexene-1.2%, 2- and 3-hexenes-68.0%, heptylaldehydes-24.8%, and heptylalcohols-5.7%. Thus, at this level of conversion the alcohols constituted 19% of the product. After 18.5 hours, another sample was withdrawn and analyzed. This analysis showed that the reaction mixture had the following composition on a molar basis: 1-hexene-0.7%, 2- and 3-hexenes-30%, heptylaldehydes-31%, heptylalcohols-32%, hexane-0.3%. Thus, the alcohols constituted 49% of the product.

EXAMPLE 22

This example will compare the effect of using a soluble, homogeneous catalyst compositionally analogous to the heterogeneous catalyst employed in the previous example and in the same reaction.

The soluble catalyst employed was composed of rhodium trichloride in combination with 4-methylbenzyldimethylamine. This catalyst was prepared by charging 0.124 g of rhodium trichloride and 1.0 g of 4-methylbenzyldimethylamine to a stirred autoclave. To the autoclave was also charged 100 ml of 2-hexene. The contents of the autoclave were heated to 100° C. and a 50/50 mixture of carbon monoxide and hydrogen was added to give a pressure of 1000 psi. This pressure was maintained between 600 and 1000 psi by periodic addition of the carbon monoxide-hydrogen mixture. After 1.6 hours, a sample of the reaction mixture was withdrawn and analyzed by vapor phase chromatography. This analysis showed that the reaction mixture had the following composition on a molar basis: 1-hexene-1.5%, 2- and 3-hexenes-59.6%, heptylaldehydes-38%. Heptylalcohols were not detected at this conversion level. After 16.3 hours, another sample was withdrawn and was found to have the following composition on a molar basis: 2- and 3-hexenes-5.0%, heptylaldehydes-84%, heptylalcohols-11%, hexane-1.6%.

At even a longer reaction time, the soluble catalyst system produced only small amounts of alcohols, i.e., 13% of the total product at 84% conversion. Thus, from the standpoint of alcohol production, the soluble catalyst system is much less effective than the insoluble catalyst system employed in the previous example.

EXAMPLE 23

This example will illustrate the results obtained employing various olefins.

The catalyst employed was the catalyst of Example 7. The reactions were carried out in a fixed bed continuous flow reactor. The olefins, reaction conditions, and results obtained are given in the table.

TABLE V

| Olefin | Temp. (°F.) | Pressure (psi) | Molar Ratio $H_2/CO/$ olefin | LHSV | % Olefin Conv. | % Selectivity to Alcohol |
|---|---|---|---|---|---|---|
| Propylene | 205 | 1500 | 2.5/1.25/1 | 0.33 | 88.8 | 98.5 |
| 1-Hexene | 200 | 2000 | 2.2/1.1/1 | 0.33 | 91.4 | 99.8 |
| 2-Hexene | 246 | 2000 | 2.2/1.1/1 | 0.33 | 98.8 | 99.6 |
| Equilibrated | 180 | 2000 | 2.2/1.1/1 | 0.33 | 47.4 | 98.1 |

TABLE V-continued

| Olefin | Temp. (°F.) | Pressure (psi) | Molar Ratio H₂/CO/ olefin | LHSV | % Olefin Conv. | % Selectivity to Alcohol |
|---|---|---|---|---|---|---|
| linear hexene isomers | | | | | | |
| 1-Octene | 250 | 2000 | 2.2/1.1/1 | 2.0 | 65 | 65 |
| 1-Dodecene[a] | 217 | 2000 | 2.2/1.1/1 | 1.2 | 75 | 87 |
| Propylene trimer | 242 | 2000 | 4/2/1 | 0.5 | 15.5 | 90 |
| 2,4,4-Trimethyl-1-pentene | 245 | 2000 | 5.8/2.9/1 | 0.4 | 23 | 86 |
| 2,5-Dimethyl-1,5-hexadiene | 227 | 2000 | 4/2/1 | 0.33 | 78 | 89[b] |

[a]16.6% by volume methanol was employed as an added solvent.
[b]The major products were monounsaturated alcohols —45% and dialcohols —23%.

EXAMPLE 24

This example will illustrate the results obtained employing cyclohexene.

The catalyst in this example was the catalyst of Example 7. An autoclave was charged with 3 g of catalyst, 90 ml of hexane, and 10 ml of cyclohexene. The contents of the autoclave were then heated to 100° C. and a 50/50 mixture of carbon monoxide and hydrogen was added to give a pressure of 1000 psi. The pressure was maintained between 900 and 1000 psi by periodic addition of the carbon monoxide-hydrogen mixture. After 19.6 hours, a sample of the reaction mixture was withdrawn and analyzed by vapor phase chromatography. This analysis showed that about 92% of the cyclohexene had been converted to cyclohexyl carbinol with a selectivity of greater than 99%.

EXAMPLE 25

This example will illustrate the effect of various added solvents.

In each of the reactions, propylene was converted to butyraldehydes and the catalyst employed was the catalyst of Example 3. The reactions were conducted in a fixed bed continuous flow reactor at a total pressure of 1000 psi. The reactants were continuously fed into the reactor in a molar ratio of 1.1/1.1/1=H₂/CO/propylene, respectively. The LHSV of the propylene was 4.0. The solvents, reaction conditions, and relative activities are given in the table.

TABLE VI

| Solvent | Volume % | % Conv. | Relative Activity |
|---|---|---|---|
| None | 0 | 9.5 | 1.0 |
| Butyl ether | 6.25 | 13.2 | 1.3 |
| Benzene | 6.25 | 14.5 | 1.7 |
| Triethylamine | 6.25 | 15.0 | 1.8 |
| Acetonitrile | 6.25 | 19.4 | 2.2 |
| 3-Pentanone | 6.25 | 20.0 | 2.2 |

TABLE VI-continued

| Solvent | Volume % | % Conv. | Relative Activity |
|---|---|---|---|
| Water | 6.25 | 30.3 | 3.6 |
| i-Butyl Alcohol | 6.25 | 49.5 | 6.9 |
| i-Butyl Alcohol | 25 | 53.4 | 7.8 |

EXAMPLE 26

This example will further illustrate the effect of added solvents.

In this example, 1-hexene was the olefin employed and the effect of the solvents on the selectivity to alcohol was measured. The reactions were conducted in a fixed bed continuous flow reactor using a catalyst prepared with procedures and materials similar to those of Example 7. The catalyst contained 0.38% by weight of rhodium. The solvents, reaction conditions, and selectivities to alcohols are given in the table.

TABLE VII

| Solvent | Volume % | Temp (°F.) | Pressure (psi) | Molar Ratio H₂/CO/ Olefin | LHSV | % Conv. | % Selectivity to Alcohol |
|---|---|---|---|---|---|---|---|
| — | — | 228 | 2000 | 2.2/1.1/1 | 0.33 | 77.8 | 36.6 |
| Methanol | 5.0 | 241 | 2000 | 3.2/1.6/1 | 1.0 | 74.0 | 57.9 |
| Methanol | 25 | 255 | 2000 | 3.2/1.6/1 | 1.0 | 77.0 | 78.6 |
| Hexanol | 25 | 229 | 2000 | 3.2/1.6/1 | 1.0 | 69.8 | 30.4 |
| Acetic Acid | 5.0 | 252 | 2000 | 3.2/1.6/1 | 1.0 | 69.3 | 75.6 |

EXAMPLE 27

This example will illustrate the effect of added solvents where the polymer portion of the catalyst is not intrinsically porous.

The catalyst employed in the first two reactions was a gel-type cross-linked polyvinylpyridine resin containing basic pyridine functional groups to which 0.46 weight percent of rhodium was bound and the catalyst employed in the last three reactions was a gel-type acrylic polymer containing tertiary amine functional groups to which 1.96 weight percent of rhodium was bound. The reactions were conducted in stirred autoclaves at 100° C. and 1000 psi with a 1:1 molar ratio of carbon monoxide and hydrogen. The olefin employed was 1-hexene and aldehydes and alcohols were formed. The table gives the solvents and other data. In the table, the swelling ratio is the expanded volume of the catalyst in the solvent to the volume of dry catalyst.

TABLE VIII

| Solvent | Solvent Volume % | Swelling Ratio | Relative Activity | % Alcohol at 40% Olefin Conv. | % Alcohol at 80% Olefin Conv. | Reaction Time (min) |
|---|---|---|---|---|---|---|
| — | 0 | 1.0 | 1 | — | 3.4 | 8390 |
| Methanol | 10 | 2.1 | 20 | — | 15 | 600 |
| — | 0 | 1.0 | 1 | 0.22 | — | 224 |
| Methanol | 50 | 2.9 | 4.6 | 8.5 | — | 47 |
| Benzene / Acetonitrile | 53.6 / 17.5 | 1.4 | 2.4 | 4 | — | 80 |

EXAMPLE 28

This example will illustrate the hydroformylation of dienes to mono-unsaturated alcohols or dialcohols.

The catalyst employed was prepared according to Example 7 with the exception that a carbon monoxide atmosphere was maintained during the catalyst synthesis. The reactions were carried out using a fixed bed continuous flow reactor packed with the catalyst. Hydrogen, carbon monoxide, the diene, and added solvent were passed downflow over the catalyst at a pressure of 2000 psi. The dienes, added solvents and the amounts thereof, reaction conditions and results obtained are given in the table.

TABLE IX

| Diene | Added Solvent | Molar Ratio $CO/H_2$/Diene | Temp (°F.) | LHSV | % Conv. | Product(s) | % Selectivity |
|---|---|---|---|---|---|---|---|
| 2,5-Dimethyl-1,5-hexadiene | — | 4/2/1 | 227 | .33 | 83 | Monounsaturated alcohol[a] | 32 |
|  |  |  |  |  |  | Dialcohol[b] | 32 |
| 2,5-Dimethyl-2,4-hexadiene | — | 4/2/1 | 244 | .33 | 12 | Saturated monoalcohol | 73 |
| 1,5-cyclo-octadiene | Methanol 20% | 6.6/3.3/1 | 240 | .25 | 83.5 | Monounsaturated alcohol[c] | 35 |
| d-Limonene | Methanol 6.1% | 4.4/2.2/1 | 244 | .36 | 51.2 | d-Monounsaturated alcohol[d] | 83.4 |
| Commercial Dipentene | Methanol 6.1% | 4.4/2.2/1 | 245 | .27 | 73.9 | Monounsaturated alcohol[d] | 71.6 |
| 4-Vinyl Cyclohexene | Methanol 20% | 2.2/1.1/1 | 183 | .75 | 93.5 | Monounsaturated alcohol[e] | 62.2 |

[a]3,6-Dimethylheptenol.
[b]Mostly 3,6-dimethyloctane-1,8-diol.
[c]Cyclooctenyl carbinol.
[d](4-Methylcyclohex-3-enyl)-3-butanol.
[e]Cyclohexenyl propanol.

EXAMPLE 29

This example will illustrate the hydroformylation of dicyclopentadiene.

A 2.1 rocking autoclave was charged with 400 ml of methanol, 1013 g of dicyclopentadiene, and 30 g of a rhodium-amine resin catalyst similar to that described in Example 7. The reaction mixture was placed under an atmosphere of a 2:1 molar ratio of hydrogen to carbon monoxide and heated to 115° C. The pressure was then raised to 1360 psi and maintained at this pressure by periodic addition of the hydrogen-carbon monoxide mixture. After 144 hours, the reactor was cooled and vented and the contents removed. The liquid product was found to have the following composition on a molar weight basis: methanol-36%, dicyclopentadiene-23%, and monounsaturated oxo alcohol product-15%.

EXAMPLE 30

This example will illustrate the hydroformylation of a commerical refinery stream containing olefins to form aldehydes.

The catalyst employed in each reaction was prepared according to Example 2 and contained 1.03% by weight of rhodium. In the first reaction, methanol was employed as an added solvent and in the second reaction iso-butyl alcohol was employed as an added solvent. The refinery stream had the following composition in weight percent: ethane-0.5, propane-37.3, propylene-61.6, and isobutane-0.6. Twenty ml of the catalyst were placed in a tubular, fixed bed, continuous flow reactor and the refinery stream, carbon monoxide, hydrogen, and solvent passed downflow over the catalyst. The reaction conditions and results obtained are given in the table.

TABLE X

| Temp (°F.) | Pressure (psi) | Molar Ratio $H_2$/CO/Olefin | LHSV | % Propylene Conv. | % Selectivity to Aldehyde[a] |
|---|---|---|---|---|---|
| 245 | 500 | 2.2/2.2/1 | 1.1 | 96 | 97.8 |
| 218 | 2000 | 1.1/1.1/1 | 4.5 | 90.3 | 99.6 |

[a]The major byproducts in these reactions were alcohols.

EXAMPLE 31

This example will be illustrative of the treatment of a butane-butene stream in accordance with the procedure of the invention.

In this example, in each reaction, a butane-butene stream containing, in weight percent, propane-5.1, propene-1.5, butane-64.7, butene-28.1, pentane-0.9, and pentene-0.1 was employed. The catalyst employed contained 1.37 weight percent of rhodium and was prepared employing a procedure similar to that of Example 7. This catalyst in the volume of 100 ml was placed in a tubular fixed bed continuous flow reactor. The butane-butene stream, hydrogen, and carbon monoxide were passed downflow over the catalyst at a total pressure of 2000 psig. The process conditions employed and the conversions obtained are set forth in the table.

TABLE XI

| Molar Ratio $H_2$/CO/Olefin | LHSV | Temp. (°F.) | % Conversion of Olefins | % Selectivity to Alcohol |
|---|---|---|---|---|
| 6.6/3.3/1 | .33 | 200 | 79 | 99+ |
| 2.6/1.3/1 | .92 | 212 | 57 | 99+ |
| 3.3/1.65/1 | .66 | 204 | 68 | 99+ |
| 2.6/1.3/1 | .92 | 195 | 48.5 | 99+ |

The combined liquid products of the four reactions had the following weight composition: unreacted butane-butene stock-9.0%, $C_4$ and $C_5$ aldehydes-0.5%, $C_4$ alcohols-5.0%, $C_5$ alcohols-85.0%, and $C_6$ alcohols-0.5%.

EXAMPLE 32

This example will be illustrative of the treatment of a light thermofor catalytic cracking gasoline fraction in accordance with the process of the invention.

The gasoline employed had a boiling range of 33°–137° C. and had the following composition:

| Component | Wt. % |
|---|---|
| Olefins | 33.2 |
| Paraffins | 58.4 |
| Aromatics | 2.4 |
| Cycloparaffins | 5.9 |
| OLEFIN COMPOSITION | |
| Butenes | 2.2 |
| Pentenes | 18.03 |
| Hexenes | 11.28 |
| Heptenes | 1.03 |
| Cycloolefins + diolefins | 0.54 |
| "Gum": | .4 mg/100 ml |
| Nitrogen | 15 ppm |
| Phosphorus | 5 ppm |
| Sulfur | 230 ppm |
| API gravity | 80 |

The catalyst employed was prepared in accordance with the procedure of Example 7 and contained 1.37% of rhodium. Reaction conditions were as follows: 235°–250° F., 2000 psig, molar ratio of hydrogen to carbon monoxide to gasoline of 1.4:0.7:1, respectively, catalyst-100 milliliters, liquid hourly space velocity-1. The conversions ranged from 88 to 94% with selectivity to alcohols of 99%. Essentially no catalyst aging was noticed during this time in spite of the presence of hetero atoms, especially sulfur, in the gasoline feed. The product was distilled and the portion which boiled between 140°–190° C. was collected. This constituted about 2000 g of a mixture of $C_6$ and $C_7$ alcohols. The residue was 36 g and was composed primarily of higher boiling alcohols.

EXAMPLE 33

This example will illustrate the hydroformylation of a refinery stream employing a catalyst comprising rhodium bound to a styrene-divinylbenzene copolymer containing phosphine functional groups.

The refinery stream employed was the same as that of Example 32. The catalyst employed contained 0.33% by weight of rhodium and was prepared by a procedure identical with that of Example 3. The reaction conditions were as follows: temperature-247° F., pressure-1550 psi, ratio of reactants-$H_2$/CO/refinery stream=1/1/1, amount of catalyst in fixed bed, continuous flow reactor-210 ml, and LHSV-0.16. The olefins in the refinery stream were converted to aldehydes and the conversion over a period of 8 days averaged 75%.

EXAMPLE 34

This example will be illustrative of the procedure of the invention as applied to the treatment of a heavy thermofor catalytic cracking gasoline in accordance with the process of the invention.

The gasoline employed had a boiling range between 270°–630° F. and contained about 22% of olefins having 6 or more carbon atoms. The catalyst employed contained 1.59% by weight of rhodium and was prepared in accordance with the precedure set forth in Example 7. Twenty-two ml of this catalyst were packed in a fixed bed continuous flow reactor and hydrogen and carbon monoxide and the gasoline in the respective ratio of 3:1.5:1 were passed downflow over the catalyst at 2000 psig and 246° F. at a liquid hourly space velocity of 0.5. The steady-state conversion level was 61%, with a selectivity of 99%, to alcohols.

EXAMPLE 35

This example will illustrate the results obtained by hydroformylation of an olefin employing a catalyst comprising rhodium bound to an ion exchange cellulose containing tertiary amine functional groups.

In this example, the catalyst of Example 8 was employed. This catalyst, in the amount of 3 g, was charged into an autoclave along with 10 ml of 1-hexene, 10 ml of methanol, and 80 ml of benzene. The contents of the autoclave were stirred and heated to 100° C. under an atmosphere of carbon monoxide. An equimolar mixture of carbon monoxide and hydrogen was added to the autoclave to give a total pressure of 1005 psig. The pressure in the autoclave was maintained between 900 and 1020 psi by periodic addition of the carbon monoxide-hydrogen mixture. After 1 hour, a sample aliquot was withdrawn and analyzed by vapor phase chromatography. The analysis showed that all of the 1-hexene had been converted to a mixture of 2- and 3-hexenes (52 weight percent of the 1-hexene product) and isomeric heptylaldehydes (48 weight percent of the 1-hexene product). After about 19 hours, another sample was withdrawn and analyzed. The analysis showed that the product composition in weight percent was as follows: hexenes-0.3, heptylaldehydes-18.6, and heptylalcohols-81.1.

What is claimed is:

1. A process for the production of an oxygenated compound selected from the group consisting of aldehydes and alcohols comprising hydroformylating an olefin with carbon monoxide and hydrogen under hydroformylating conditions at a temperature up to about 250° C. and with a catalyst consisting essentially of an insoluble organic polymer containing a functional group selected from the group consisting of amine, thiol, phosphine and arsine groups having chemically bonded thereto a metal selected from the group consisting of cobalt and rhodium.

2. The process described in claim 1 wherein said organic polymer is a copolymer of styrene and divinylbenzene.

3. The process described in claim 1 wherein said functional group is an amine group.

4. The process described in claim 2 wherein said functional group is an amine group.

5. The process described in claim 1 wherein said functional group is a phosphine group.

6. The process described in claim 2 wherein said functional group is a phosphine group.

7. The process described in claim 1 or 2 or 3 or 4 or 5 or 6 wherein said chemically bonded metal is rhodium.

* * * * *